US006809071B2

(12) United States Patent
Hasegawa et al.

(10) Patent No.: US 6,809,071 B2
(45) Date of Patent: Oct. 26, 2004

(54) METHOD OF MANUFACTURING SOAP WITH AIR BUBBLES

(75) Inventors: Takeshi Hasegawa, Tokyo (JP); Yasunori Miyamoto, Tokyo (JP); Tadao Abe, Tokyo (JP); Koichi Hatano, Tochigi (JP)

(73) Assignee: Kao Corporation, Tokyo (JP)

( * ) Notice: Subject to any disclaimer, the term of this patent is extended or adjusted under 35 U.S.C. 154(b) by 209 days.

(21) Appl. No.: 10/130,608

(22) PCT Filed: Sep. 20, 2001

(86) PCT No.: PCT/JP01/08175

§ 371 (c)(1), (2), (4) Date: Jun. 27, 2002

(87) PCT Pub. No.: WO02/24856

PCT Pub. Date: Mar. 28, 2002

(65) Prior Publication Data

US 2003/0096719 A1 May 22, 2003

(30) Foreign Application Priority Data

Sep. 22, 2000 (JP) ........................................ 2000-289622
Sep. 22, 2000 (JP) ........................................ 2000-289623

(51) Int. Cl.[7] .................................................. A61K 7/50

(52) U.S. Cl. .......................... 510/145; 510/152; 264/51; 264/211.11; 264/325; 264/334; 425/548; 422/129.1

(58) Field of Search ................................ 510/145, 147, 510/152; 264/211.11, 334, 325, 51; 425/548; 422/129.1

(56) References Cited

FOREIGN PATENT DOCUMENTS

| | | |
|---|---|---|
| CA | 2037310 | 9/1991 |
| JP | 10-195494 | 7/1998 |
| JP | 11-43699 | 2/1999 |

*Primary Examiner*—Necholus Ogden
(74) *Attorney, Agent, or Firm*—Oblon, Spivak, McClelland, Maier & Neustadt, P.C.

(57) ABSTRACT

A method of producing aerated soap 5 comprising solidifying molten soap 4 having bubbles dispersed therein in a molding unit, wherein a storage tank 61 of the molten soap 4 has a circulating duct 62 forming a loop passing through the storage tank 62, and the circulating duct 62 or the storage tank 61 has connected thereto a feed nozzle 31 for feeding the molten soap 4, whereby the molten soap 4 is fed to the molding unit through the feed nozzle 31 while being circulated in the circulating duct 62.

12 Claims, 3 Drawing Sheets

METHOD OF MANUFACTURING SOAP WITH AIR BUBBLES

TECHNICAL FIELD

The present invention relates to a method of producing aerated soap from aerated molten soap. More particularly, it relates to a method of producing aerated soap while preventing separation of the molten soap into gas and liquid.

BACKGROUND ART

Applicant of the present invention has previously proposed in JP-A-10-195494 a method of producing aerated soap which comprises solidifying molten soap containing a large number of bubbles in a cavity of a mold, wherein the step of solidification is carried out in a hermetically closed cavity.

According to this production method, outside air not being allowed to enter the cavity, the solidified soap hardly suffers from void or depression development. However, when the operation of aerated soap production is suspended in case of some trouble, molten soap stagnates in the feed piping or the storage tank. Meanwhile the bubbles gather to gain in diameter, resulting in separation into gas and liquid. If the operation is resumed in this state, the molten soap would be injected into the cavity with gas separated from liquid. It follows that the resulting soap has bubbles dispersed non-uniformly and reduced latherability on use. Where a stirring wing (stirring blade) is used, which is the most common means of agitation, it would be difficult to break the gathered bubbles to restore a gas/liquid dispersed system at a low shearing force, or air would be entrained at too high a shearing force, causing a change in specific gravity of the molten soap. Further, variation in the state of bubbles (especially the amount of bubbles) can result in variation in the weight of solidified soap.

DISCLOSURE OF THE INVENTION

Accordingly, an object of the present invention is to provide a method of producing aerated soap while preventing separation of molten soap having a great number of bubbles dispersed therein into gas and liquid.

Another object of the present invention is to provide a method of producing aerated soap which secures uniform dispersion of bubbles and minimizes weight variation among solidified soap products.

The present invention accomplishes the above objects by providing a method of producing aerated soap which comprises solidifying molten soap having a large number of bubbles dispersed therein in a molding unit, wherein

- a circulating duct is connected to a storage tank of the molten soap to form a loop passing through the storage tank,
- the circulating duct or the storage tank has connected thereto a feeding section for feeding the molten soap, and
- the molten soap is fed to the molding unit through the feeding section while being circulated through the circulating duct.

The present invention also provides an apparatus for producing aerated soap which is used to carry out the above-described method of producing aerated soap, which comprises a storage tank for molten soap, a circulating duct connected to the storage tank and forming a loop passing through the storage tank, a molten soap feeding section which is connected to the circulating duct or the storage tank, and a molding unit where the molten soap fed from the feeding section is molded and solidified into a prescribed shape.

BEST MODE FOR CARRYING OUT THE INVENTION

Figure 1:
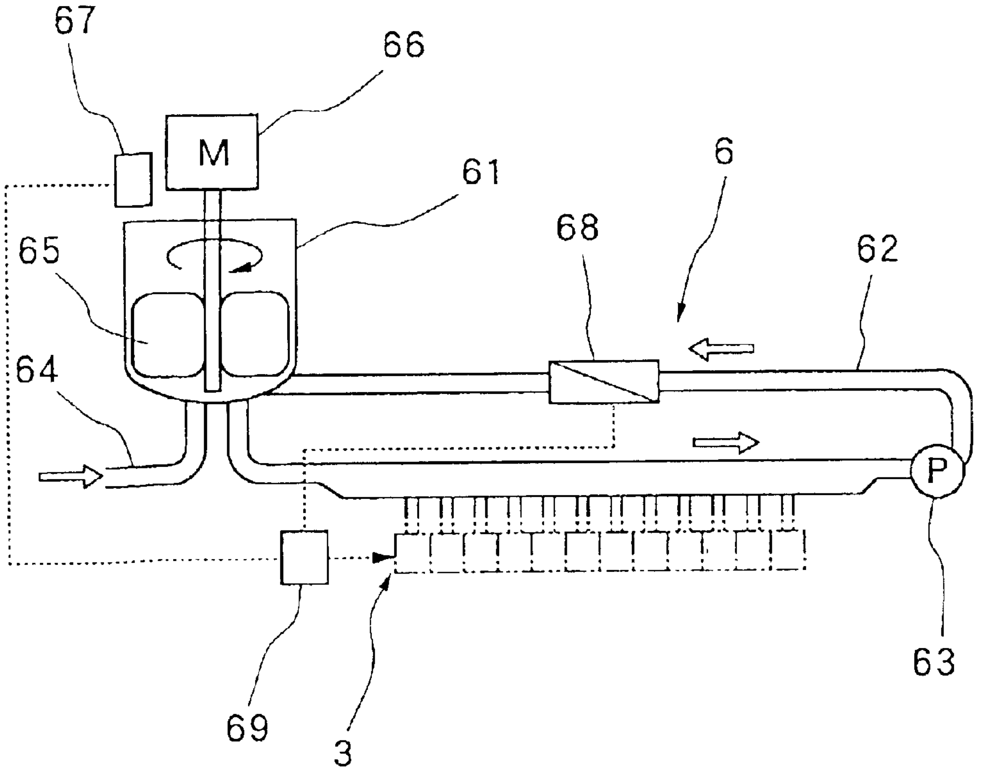
FIG. 1 is a sketch of the molten soap circulating section of an apparatus used in a first embodiment of the production method according to the present invention.
Figure 2:
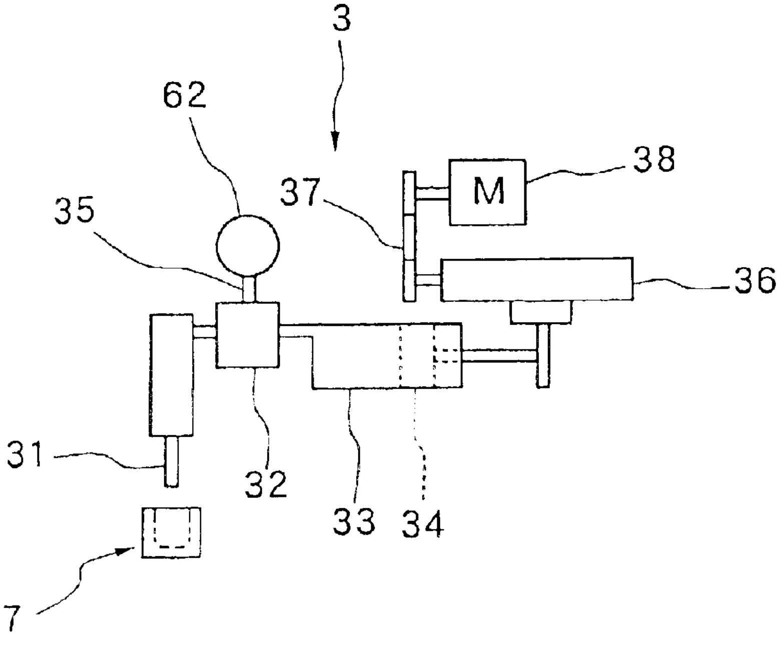
FIG. 2 is a sketch of the molten soap feeding section of an apparatus used in an embodiment of the production method according to the present invention.
Figures 3A, 3B, 3C:
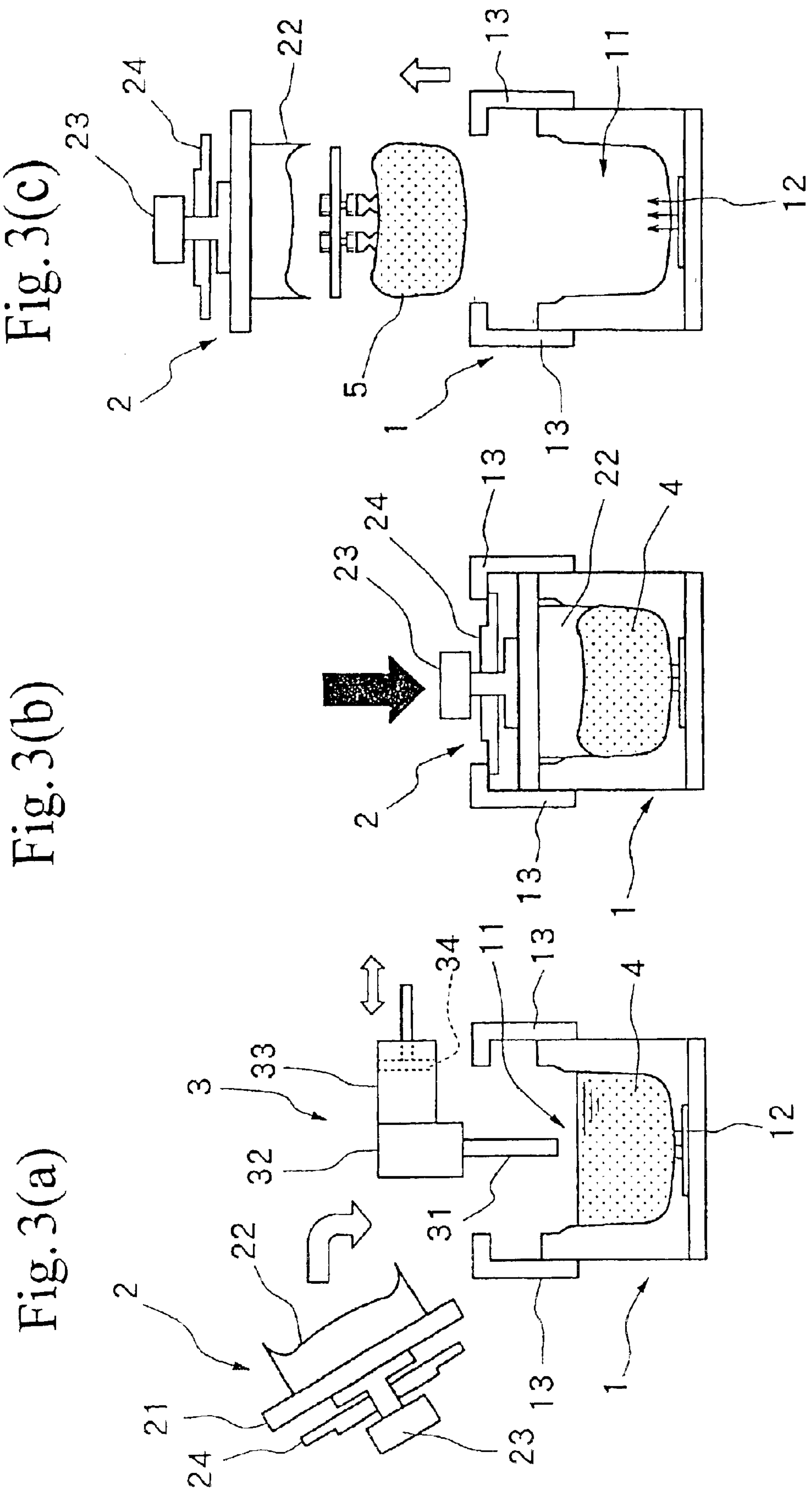
FIG. 3(*a*), FIG. 3(*b*), and FIG. 3(*c*) are sketches of the molten soap molding section of an apparatus used in an embodiment of the production method according to the present invention.

The present invention will be described with reference to its preferred embodiments by referring to the accompanying drawings. A production apparatus used in the present embodiment has a molten soap circulating section, a molten soap feeding section which is connected to the circulating section, and a molding section having a mold for molding molten soap fed from the feeding section. FIG. 1 shows the molten soap circulating section in the apparatus used in the first embodiment of the production method according to the present invention. FIG. 2 shows the molten soap feeding section, and FIG. 3 shows the molten soap molding section.

The molten soap circulating section 6 shown in FIG. 1 has a storage tank 61, a circulating duct 62 connected to the storage tank 61 and forming a closed loop passing through the storage tank 61, and a circulating pump 63 provided in the circulating duct 62. A feed duct 64 for feeding molten soap having been aerated in a aerating section (not shown) is connected to the storage tank 61. Stirring blades 65 are provided in the storage tank 61. The stirring blades 65 are driven by a motor 66 to revolve in a prescribed direction. A liquid level meter 67 is disposed above the storage tank 61. The liquid level meter 67 which can be used includes optical, ultrasonic or differential-pressure type liquid level sensors. A specific gravity meter 68 is provided in the course of the circulating duct 62. The specific gravity meter 68 which can be used includes, for example, a Coriolis mass flow sensor supplied by Sakura Endless K.K. The specific gravity can be measured in a density measurement mode. To the circulating duct 62 is connected a molten soap feeding section 3. The molten soap flow from the circulating duct 62 to the feeding section 3 is switched on and off. A plurality of feeding sections 3 are connected to the circulating duct in series. Both the circulating section 6 including the storage tank 61 and the circulating duct 62 and the feeding section 3 are maintained at a prescribed temperature with a heat retaining means such as warm water or a heater.

The liquid level of molten soap measured with the liquid level meter 67 and the molten soap density measured with the specific gravity meter 68 are each converted into electrical signals and sent to a computing unit 69, where calculations for controlling the operation of a servo motor 38 are carried out based on the molten soap liquid level and density data, and the calculation results are converted to electrical signals and sent to the servo motor 38.

Circulation of molten soap in the circulating section having the above-mentioned constitution will be described. Molten soap that has been aerated in the aerating section (not shown) to have a large number of bubbles dispersed therein is supplied to the storage tank 61 through the feed duct 64 and stored there. The molten soap is stirred in the storage tank 61 by means of the stirring blades 65 to keep a uniform bubble-dispersed state. Part of the molten soap is delivered to the circulating duct 62 by means of the circulating pump 63. As a result, the molten soap stored in the storage tank 61 circulates through the circulating duct 62 while passing through the storage tank 61. By this circulation the molten soap is prevented from stagnating in the feed piping even when the operation of aerated soap production is suspended in case of some trouble, whereby shearing force is always exerted on the aerated molten soap to prevent separation into gas and liquid. In the present embodiment, in particular, since shearing force is applied to the molten soap by the circulation, there is an advantage that the time of applying the shearing force to molten soap is controllable through adjustment of, for example, the flow velocity of the molten soap. That is, maintaining aerated molten soap, which is a compressive fluid having low storage stability, under shearing force for a long period of time makes it possible to change the state of bubbles. With no shearing force applied, gathering of bubbles or separation into gas and liquid occurs unavoidably. Thus, a shearing force can be exerted on the molten soap in an effective manner by controlling the time of shearing force application while the molten soap is circulated. As a result, the bubbles can be kept in a satisfactory dispersed state in the molten soap in the storage tank 61, and the satisfactory state can be maintained for a prolonged period of time. Separation into gas and liquid is suppressed to some extent by the stirring with the stirring blades 65 in the storage tank 61, which cannot be seen as sufficient. If the molten soap is agitated with the stirring blades 65 to a sufficient degree for preventing gas-liquid separation or gathering of bubbles, the molten soap would entrain air bubbles, resulting in variation of specific gravity of the molten soap. Therefore, it is desirable that the stirring in the storage tank 61 be so mild as to avoid air entrapment and that prevention of gas-liquid separation be achieved by circulation in the circulating duct 62.

While the molten soap circulates, its density is measured with the specific gravity meter 68 and, at the same time, the molten soap liquid level in the storage tank 61 is measured with the liquid level meter 67.

Molten soap having a great number of bubbles dispersed therein can be prepared by, for example, the method described in JP-A-11-43699, filed by the present applicant, col. 2, line 15 to col. 5, line 1. Various gases are useful for aerating molten soap. In particular, an inert gas, especially a non-oxidizing inert gas such as nitrogen gas, is effective to prevent the molten soap components from being oxidatively decomposed on heating to generate offensive odors, etc. Use of an inert gas for aeration is particularly effective where a perfume component susceptible to oxidative decomposition is compounded as a component of aerated soap.

It is preferred that the circulating molten soap be maintained at a temperature of 55 to 80° C., particularly 60 to 70° C., to prevent the molten soap from solidifying at the tip of feed nozzles hereinafter described and to prevent oxidation of soap and deterioration of perfume.

In this connection, the circulating molten soap is preferably heated to and maintained at a temperature higher than the melting point by 1 to 20° C., particularly 2 to 5° C., for the same reason.

Circulation of the molten soap is preferably such that the ratio of the storage tank 61 capacity S ($m^3$) to the circulating flow rate V ($m^3$/hr), S/V ratio (hr), be in the range of from 0.01 to 5 in order to prevent bubbles' gathering and separation into gas and liquid.

In connection to the circulating flow rate, the molten soap is preferably circulated in the circulating duct 62 at a flow velocity Vd of 0.02 to 5 m/s, particularly 0.05 to 0.8 m/s. Below the lower limit, a pressure drop occurs easily when the molten soap is dispensed to the feeding section 3. Above the upper limit, the equipment must have an increased scale, and there is a high possibility that the molten soap entraps air bubbles while circulated. For the same reasons, the circulating duct 62 preferably has a cross sectional area of 10 to 200 $cm^2$, particularly 20 to 180 $cm^2$.

The molten soap being circulated preferably has a shear rate of 0.2 to 500 $s^{-1}$, particularly 0.3 to 100 $s^{-1}$, especially 0.3 to 20 $s^{-1}$, to prevent bubbles' gathering and separation into gas and liquid. The shear rate D is calculated from D=2 Vd/d, wherein Vd is a circulating flow velocity (m/s) of the molten soap, and d is the diameter (m) of the circulating duct 62. It is preferred to appropriately dispose a static mixer in the circulating duct for applying shear within the above shear rate range.

Part of the molten soap circulating in the circulating duct 62 is dispensed to the feeding section 3 connected to the circulating duct 62. As shown in FIG. 2, the feeding section 3 has a connecting pipe 35 one end of which is connected to the circulating duct 62, a switch valve 32 connected to the other end of the connecting pipe 35, a feed nozzle 31 connected to one end of the switch valve 32, a cylinder 33 connected to the other end of the switch valve 32, and a piston 34 disposed in the cylinder 33. The switch valve 32 switches on and off the connection between the circulating duct 62 and the feed nozzle 31. The rod of the piston 34 has a linear guide 36 attached to the rear end thereof. The linear guide 36 is connected to the servo motor 38 via a linking mechanism 37. The servo motor 38 operates to make the linear guide 36 take a linear and reciprocal motion, thereby causing the piston 32 to slide back and forth in the cylinder 33. The volume of the molten soap to be fed is decided by the draw or push distance of the piston 34. Specifically, the volume to be fed is decided by (1) a method in which the piston position before suction is taken as an origin, and the feed volume is decided from the draw-back distance of the piston or (2) a method in which the piston position after suction is taken as an origin, and the feed volume is decided from the push distance of the piston. Since the molten soap to be metered is a compressive fluid, it is preferred for obtaining improved precision of measured weight to use the method (1) and decide the origin so that the amount of the molten soap remaining in the cylinder when the piston is at the origin may be minimized. The servo motor 38 is controlled based on the calculations in the computing unit 69 as stated above. The details of the control will be described later.

The molten soap flow in the feeding section 3 will then be described. On switching the switch valve 32, part of the molten soap circulating in the circulating duct 62 is delivered into the cylinder 33 through the connecting pipe 35 and the circulating duct 62. At this time, the piston 34 may have been pulled back to a prescribed position by the linear guide 36. Alternatively, the piston 34 may be pulled back gradually with the molten soap feed into the cylinder 33.

On dispensing a prescribed amount of the molten soap to the cylinder 33, the flow is switched over by the switch valve 32 to connect the cylinder 33 and the feed nozzle 31. Then, the piston 34 is pushed over a prescribed distance by the linear guide 36 to push the molten soap out of the cylinder 33, whereby the molten soap is fed through the feed nozzle 31 to the molding section 7 as a molding unit. There are provided as many molding sections 7 as the feed nozzles 31. The above-described series of operations are carried out in every feeding section 3.

The travel of the piston 34 is decided under control by the servo motor 38 based on the calculations from the molten soap density measured with the specific gravity meter 68 and the molten soap liquid level in the storage tank 61 measured with the liquid level meter 67. More specifically, the following operations are performed.

As for the molten soap density, the correlation between a weight A of the molten soap fed to the molding section 7 and a density $\rho$ of the molten soap is obtained beforehand. The present inventors' study have revealed that these variables depict an ascending linear plot. A coefficient obtained from this linear relationship is taken as $C_\rho$. In the similar manner, the correlation between a molten soap weight A fed to the molding section 7 and the molten soap liquid level L is obtained beforehand. The present inventors' study have revealed that these variables also depict an ascending linear plot. A coefficient obtained from this linear relationship is taken as $C_L$. The molten soap weight $A_0$ that is to be fed to the molding section 7 is previously set. The density $\rho_0$ and the liquid level $L_0$ of the molten soap which correspond to the set weight $A_0$ are previously obtained from the above-described linear relationships. These $C_\rho$, $C_L$, $A_0$, $\rho_0$, and $L_0$ values are inputted in the computing unit 69 as initial values.

Then the difference between $\rho_m$ and $\rho_0$ ($\Delta\rho=\rho_m-\rho_0$) and the difference between $L_m$ and $L_0$ ($\Delta L=L_m-L_0$) are calculated in the computing unit 69 based on the previously obtained $\rho_0$ and $L_0$ values and the molten soap density $\rho_m$ and liquid level $L_m$ obtained by measurement. The calculated $\Delta\rho$ and $\Delta L$ are each multiplied by the respective constants, $C_\rho$ and $C_L$, which have been inputted as initial values, to obtain a weight corrected from the set weight $A_0$, i.e., ($C_\rho\Delta\rho+C_L\Delta L$). Division of the corrected weight by the measured density $\rho_m$ gives a corrected volume. The cross sectional area of the cylinder 33 being known, the corrected volume is divided by the cross sectional area to give a corrected travel of the piston 34. The thus calculated corrected travel is converted to a rotation step of the servo motor 38, and the converted value is sent to the servo motor 38 to control the piston 34 travel.

By this series of operations a constant weight of the molten soap can be poured into the molding section 7 irrespective of molten soap density variations made by some causes. Further, since the molten soap is kept circulated, it does not stagnate in the course from aerating to feeding in case of suspension of the operation and is thereby prevented from separating into gas and liquid. As a result, the resulting aerated soap has bubbles uniformly dispersed therein and lathers well on use.

Molding of the molten soap fed to the molding section 7 is illustrated by referring to FIGS. 3(*a*) to 3(*c*). As shown in FIG. 3(*a*), the molding section 7 has a lower mold 1 and an upper mold 2 making a mold. The lower mold 1 is made of a rigid material such as metal and has a cavity 11 facing up. The cavity 11 has a concave shape in agreement with the bottom and sides of an aerated soap as a product. A plurality of interconnecting holes 12 are made in the bottom of the cavity 11 which interconnect the cavity 11 and the outside of the lower mold 1. A clamping mechanism 13 is attached to the sides of the lower mold 1 which clamps the lower mold 1 and the upper mold 2.

The upper mold 2 is also made of a rigid material such as metal. The upper mold 2 is composed of a lid 21, a compressing part 22 which is fitted to the lower side of the lid 21 and the lower side of which is shaped to the upper contour of the aerated soap, a pressing part 23 fitted to the upper side of the lid 21, and a fitting part 24 which is fitted to the pressing part 23 with play and engaged with the clamping mechanism 13 of the lower mold 1.

As shown in FIG. 3(*a*), molten soap 4 injected from the feed nozzle 31 is poured into the cavity 11 of the lower mold 1. It is preferred that the volume of the molten soap 4 supplied under the above-described control by the computing unit 69 be at least 1.05, particularly 1.1, time the target volume of an aerated soap as a product. This is favorable for effectively preventing shrinkage or development of sink marks on cooling the molten soap in cooperation with compression of the molten soap (hereinafter described). In order to achieve such a relationship, the density of the molten soap is adjusted properly. The upper limit of the molten soap volume to be fed is decided appropriately in accordance with the volumetric proportion of bubbles in the molten soap. For example, where the total volume of bubbles in the molten soap volume is relatively large, the degree of shrinkage on cooling will be high so that the upper limit of the volume to be fed is set relatively high. Where the total volume of bubbles in the molten soap volume is relatively small, on the other hand, since the degree of shrinkage on cooling is not so high, the upper limit of the volume to be fed is set relatively low. Considering that the total volume of bubbles is about 5 to 70% of the molten soap volume in this particular embodiment, the upper limit of the volume to be fed is preferably three times, particularly twice, the volume of an aerated soap. While the volume of molten soap varies depending on pressure and temperature, this term as referred to herein means the volume at 25° C. under atmospheric pressure.

The temperature of the molten soap poured into the cavity 11 is practically the same as that of the molten soap circulating in the circulating duct 62.

Upon completion of feeding the molten soap 4, the upper side of the lower mold 1 is closed with the upper mold 2, and the fitting part 24 fitted to the upper mold 2 is engaged by the clamping mechanism 13 attached to the lower mold 1. Thus, the two molds are fixed to make the cavity 11 hermetic. Then, as shown in FIG. 3(*b*), the pressing part fitted to the upper mold 2 is pressed down by a prescribed pressing means (not shown), such as a pressure cylinder, to compress the molten soap in the cavity 11 to a set volume of an aerated soap as a product, and the molten soap is let to solidify in this compressed state. These operations effectively prevent development of shrinkage and sink marks on cooling to provide cakes of aerated soap with satisfactory appearance.

The pressure (gauge pressure) for compressing the molten soap is usually about 0.005 to 0.3 MPa, particularly about 0.05 to 0.2 MPa, while varying according to how many times as much as the set volume of an aerated soap the fed molten soap volume is.

The compression ratio of the molten soap, i.e., the compression ratio of the gaseous components in the molten soap (volume of gaseous components before compression/volume of gaseous components after compression) is preferably 1.08 to 2.5, still preferably 1.1 to 2, from the standpoint of preventing development of shrinkage or sink marks on cooling, reducing the cooling time, and improving productivity. The gaseous components in the molten soap include the gas used for aerating molten soap, steam contained in molten soap, and the like.

The time of solidifying the molten soap may be shortened by cooling the lower mold by a prescribed means, for example, a coolant such as water. As a matter of course, spontaneous cooling will do. Where the mold is cooled with water, the water temperature is preferably about 5 to 25° C. for preventing non-uniform dispersion of bubbles on cooling.

The molten soap is preferably solidified so that the resulting cakes of aerated soap may have an apparent density of 0.4 to 0.85 g/cm$^3$, particularly 0.6 to 0.8 g/cm$^3$. This is preferred for securing the fluidity of the molten soap, improving the cooling efficiency, improving releasability of the resulting cake from the cavity 11, and improving the appearance of the cake. Such a solidified state can be achieved by, for example, injecting aerated molten soap made of 55 ml (under atmospheric pressure) of nitrogen gas and 90 ml of a soap composition into the cavity 11 at 64° C., compressing the aerated molten soap to 120 ml, and letting the molten soap to solidify in this compressed state. The method of measuring the apparent density of aerated soap will be described in Examples hereinafter given.

It is also preferred that the molten soap is solidified in such a manner that the proportion of bubbles (pores) having a size of 1 to 300 $\mu$m in the total pore volume in the resulting aerated soap (hereinafter referred to as a pore volume fraction) may be 80% or more for improving lathering and preventing the soap from getting sodden or swollen in contact with water. Such a solidified state can be obtained by aerating a soap composition by means of, for example, an aeration apparatus Euromix MDFO supplied by Ebara Corp. at a rotor's rotation speed of 1000 kPa (500 rpm), and solidifying the thus aerated molten soap in the cavity by cooling while keeping the molten soap in a compressed state. The method of measuring the pore volume fraction of aerated soap will be described in Examples hereinafter given.

On completion of solidification of the molten soap, the engagement of the clamping mechanism attached to the lower mold 1 and the fitting part 24 attached to the upper mold 2 is released, and the upper mold 2 is removed as shown in FIG. 3(*c*). The aerated soap is taken out of the cavity 11 of the lower mold 1 by using a prescribed holding means, for example, a vacuum gripper. To facilitate removal of the aerated soap from the mold, gas such as air may be blown into the cavity 11 through the interconnecting holes 12 made in the bottom of the cavity 11.

The aerated soap thus obtained has bubbles dispersed therein uniformly and therefore lathers well. Further, the aerated soap assumes a satisfactory outer appearance with neither shrinkage nor sink marks which may have developed on cooling. In addition, the weight of the aerated soap substantially agrees with the set weight.

Compounding components which can make up the aerated soap include fatty acid soaps, nonionic surface active agents, inorganic salts, polyols, non-soap type anionic surface active agents, free fatty acids, perfumes, and water. If desired, such additives as antimicrobials, pigments, dyes, oils, and plant extracts, can be added appropriately.

Figure 4:
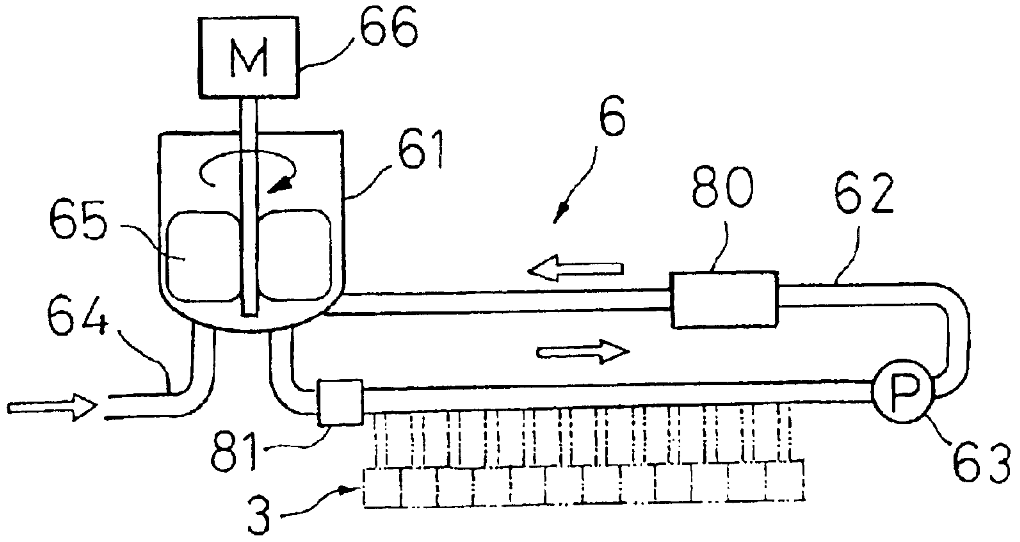
FIG. 4 is a sketch of the molten soap circulating section of an apparatus used in a second embodiment of the production method according to the present invention (corresponding to FIG. 1).
Figure 5:
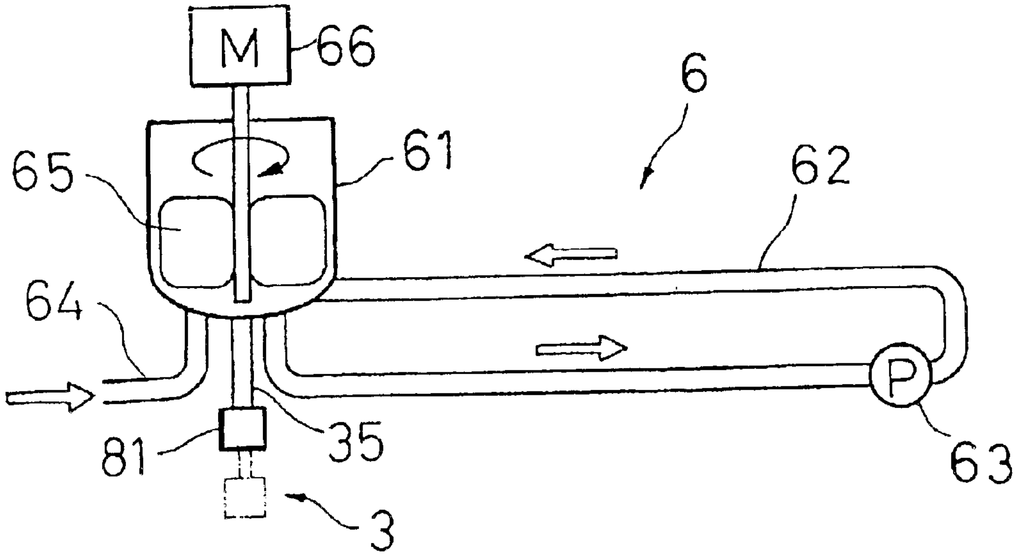
FIG. 5 is a sketch of the molten soap circulating section of an apparatus used in the second embodiment of the production method according to the present invention (corresponding to FIG. 1).

The second and the third embodiments of the present invention will be described with reference to FIGS. 4 and 5. These embodiments will be described only with reference to differences from the first one. With reference to the particulars that are not described hereunder, the description on the first embodiment applies appropriately. In FIGS. 4 and 5 the same members as in FIGS. 1 to 3 are given the same numerals as used in FIGS. 1 to 3. The liquid level meter 67, the specific gravity meter 68, and the computing unit 69 that are depicted in FIG. 1 are omitted from FIGS. 4 and 5.

In the second embodiment shown in FIG. 4, the apparatus for producing aerated soap has a cooling unit 81 provided between the storage tank 61 and the feeding section 3 for cooling the molten soap circulating in the circulating duct 62. More specifically, the cooling unit 81 is fitted to the circulating duct 62 at a position between the storage tank 61 and the position where the feeding section 3 is connected to the circulating duct 62. The cooling unit 81 is fitted immediately in front of the position where the feeding suction 3 is connected to the circulating duct 62. The circulating duct 62 also has a heating unit 80 for heating molten soap circulating through the circulating duct 62. The position of fitting the heating unit 80 is below the position where the feeding section 3 is connected to the circulating duct 62. That is, the circulating duct 62 has the cooling unit 81 in the upper reaches and the heating unit 80 in the lower reaches in the molten soap circulating direction, and the molten soap feeding section 3 is connected to a position between the cooling unit 81 and the heating unit 80 fitted to the circulating duct 62. The heating temperature by the heating unit 80 is set higher than the temperature of the circulating duct 62 so that the temperature of the molten soap returning to the storage tank 61 from the circulating duct 62 may be the same as the temperature of the molten soap stored in the storage tank (hereinafter referred to as a retained temperature). On the other hand, the cooling temperature by the cooling unit 81 is set lower than the retained temperature of a heat retaining unit which retains the circulating duct 62 warm. Thus, the molten soap is cooled to a temperature lower than the retained temperature by, for example, about 0.5 to 10° C. As a matter of course, the cooling temperature is at or above the melting temperature of soap. A heat exchanger, etc. can be used as the heating unit 80. A water-cooling pipe, etc. can be used as the cooling unit 81.

According to this embodiment, since the molten soap is cooled to a temperature lower than that of the circulating molten soap (retained temperature) before it is injected into the cavity 11 of the molding section 7, there is an advantage that the time for cooling for solidification in the cavity 11 is made shorter than in the first embodiment. When, in particular, the molten soap is cooled to a temperature lower than the retained temperature by 0.5 to 10° C. immediately before being fed into the cavity 11, the time for keeping the molten soap still in the cavity 11 where neither agitation nor shearing is applied can be reduced. As a result, occurrence of bubbles' gathering and gas-liquid separation which might occur until solidification completes can be reduced. It is to be noted, however, that cooling molten soap by the cooling unit 81 is liable to involve the fear that the fluidity of the molten soap in the circulating duct 62 reduces, failing to secure smooth circulation of the molten soap. Therefore, the heating unit 80 for heating the molten soap is provided apart from the heat retaining unit for the circulating duct 62. It is provided at a position below the position where the feeding section 3 is connected to the circulating duct 62, thereby securing smooth circulation of the molten soap.

In the third embodiment shown in FIG. 5, the feeding section 3 is not connected to the circulating duct 62 of the circulating section 6 in the apparatus for producing aerated soap. The heating unit and the cooling unit are not provided, either. Instead, the feeding section 3 is connected to the storage tank 61 through a connecting pipe 35 which is connected to the storage tank 61 apart from the circulating duct 62. A cooling unit 81 is fitted to the connecting pipe 35 which connects the storage tank 61 and the feeding section 3. In other words, the cooling unit 81 is fitted between the storage tank 61 and the feeding section 3. While FIG. 5 shows only one feeding section 3, a plurality of feeding sections can be connected to the storage tank 61. In that case, every pipe connecting each feeding section and the storage tank 61 is provided with the cooling unit. In either case, the cooling temperature by the cooling unit 81 is set lower than the retained temperature of the heat retaining unit which keeps the storage tank 61 warm. In this way, the molten soap is cooled to a temperature lower than the retained temperature by about 0.5 to 10° C.

According to this embodiment, since the molten soap is cooled to a temperature lower than that of the circulating molten soap before it is injected into the cavity 11 of the molding section 7, there is an advantage that the time for cooling for solidification in the cavity 11 is shorter than in the first embodiment similarly to the second embodiment. Additionally, because the circulating duct 62 is not cooled unlike the second embodiment, the heating unit used in the second embodiment is not needed, which simplifies the structure of the production equipment.

The present invention is not limited to the above-described embodiments. For example, while in the first and second embodiments a plurality of feeding sections 3 are connected in series to the circulating duct 62 forming a loop, a plurality of circulating ducts each forming a loop can be connected to the storage tank 61, and one or more than one feeding sections 3 are connected to each circulating duct. That is, one or more than one feed nozzles are fitted to each circulating duct, and as many lower molds as the feed nozzles can be used. According to this system, particularly where each circulating duct has only one feed nozzle, the number of revolutions of the pump can be adjusted individually unlike the series connection, which brings about the merit that the accuracy of weight to be injected can further be improved.

While in the above embodiments aerated soaps are produced by the use of the lower mold 1 and the upper mold 2, the lower mold 1 may be a split mold composed of a plurality of pieces according to the contour of a desired aerated soap product.

In the above-described embodiments, the volume of the molten soap to be fed is adjusted based on the variations in both the molten soap density and the molten soap liquid level in the storage tank 61. Instead of this, adjustment based only on variations in molten soap density is enough to produce aerated soap of constant weight. This is because the variations in molten soap density is more influential on the variations of molten soap volume than the variations in molten soap liquid level in the storage tank 61. It is, as a matter course, more favorable for precise weight control that the volume of the molten soap to be injected be adjusted based on both parameters.

While the density of the molten soap is measured in the circulating duct 62 between the storage tank 61 and the feeding section 3 in the above embodiments, the position of measurement is not limited thereto, and measurement can be made at any other position between the storage tank 61 and the feed nozzle 31. The former position is preferred, though, in view of the stabilized flow of the molten soap which will lead to reduced variations in feed.

While in the above embodiments the molding unit for aerated soap uses a mold composed of the lower mold 1 and the upper mold 2, a molding unit having other configurations and/or structures may be used. For example, the mold used in the above-described embodiments may be replaced with a hollow member made of a synthetic resin such as polyethylene, polypropylene, polycarbonate or polyester; a flexible thin metal plate; a flexible rubber material, etc., in which molten soap is fed and solidified. In this case, there is an advantage that the hollow member serves as a packaging container of the resulting aerated soap.

The mold composed of the lower mold 1 having a depression and the upper mold 2 closing the depression, which is used in the above-described embodiments, can be replaced with a split mold made up of a plurality of pieces, the pieces being combined to form a cavity in conformity to the contour of a desired aerated soap product. In using such a mold, molten soap is injected into the mold in the same manner as in injection molding of plastics.

EXAMPLES 1 TO 6 AND COMPARATIVE EXAMPLE 1

Molten soap having a great number of bubbles dispersed therein was prepared from the compounding components shown in Table 1 below in accordance with the method described in JP-A-11-43699 supra. Nitrogen gas was used for aeration.

TABLE 1

| Compounding Component of Molten Soap | Part by Weight |
|---|---|
| sodium laurate | 30.0 |
| sodium cocoyl isetionate | 2.0 |
| sodium lauroyl lactate | 5.0 |
| polyoxyethylene monolaurate | 2.0 |
| lauric acid | 5.0 |
| glycerol | 20.0 |
| sodium chloride | 1.5 |
| perfume | 1.5 |
| water | 32.0 |

Aerated soaps were produced from the prepared molten soap according to the steps shown in FIGS. 1 through 3 in Examples 1 to 6. The weight of the aerated soap was set at 90 g/cake. The molten soap storage tank 61 had a capacity of 0.2 $m^3$, and the circulating duct 62 had a cross sectional area of 78.5 $cm^2$. The circulating temperature, circulating flow rate V, circulating flow velocity Vd, tank capacity S to circulating flow rate V ratio, S/V, and shear rate D of the molten soap were as shown in Table 2. In Comparative Example 1, the molding section 7 was directly connected to the outlet of the storage tank 61 so that the molten soap was not circulated. In each of Examples and Comparative Example, the production line was once suspended for 2 hours, and the operation was resumed according to the following procedure.

The molten soap was injected into the cavity 11 of the lower molds 2 through the respective feed nozzles 31. The upper side of each lower mold 1 was closed with the upper mold 2 to make the cavity 11 hermetic, and the molten soap was compressed to a set volume (120 $cm^3$) by the compressing part 22 of the upper mold 2. The compression ratio of the molten soap was as shown in Table 2. In this compressed state the lower mold 1 was cooled with cooling water at 5 to 15° C. for 3 to 15 minutes to solidify the molten soap.

On completion of solidification of the molten soap, the upper mold 2 was removed. The aerated soap was taken out of each cavity 11 by means of a vacuum gripper while blowing compressed air into the cavity 11 through the interconnecting holes 12 made through the bottom of the cavity 11. There were thus obtained aerated soaps as final products.

The resulting aerated soaps were weighed, and their apparent density and pore volume fraction were measured according to the following methods. Further, the dispersed state of bubbles and the outer appearance of the soap were evaluated based on the following standards. The results obtained are shown in Table 2.

Measurement of Apparent Density

A rectangular parallelopiped specimen having known side lengths (e.g., 10 to 50 mm) was cut out of the resulting aerated soap and weighed. The weight was divided by the volume to give the apparent density. The volume was calculated from the three side lengths. The weight measurement was made with an electron balance. The measurement was made at 25° C.±3° C. and a relative humidity of 40 to 70%.

Measurement of Pore Volume Fraction

An aerated soap was rapidly cooled to −196° C. and cut at −150° C. The cut surface was observed in vacuo at −150° C. under an electron microscope Crio SEM JSM-5410/CRU, manufactured by JEOL Hightech Co., Ltd. The accelerating voltage was 2 kV, and a secondary electron image was used as detection signals. The diameter of pores was measured on a micrograph (magnification 500×), and a pore volume fraction was calculated from the measured diameter.

Evaluation of Dispersed State of Bubbles

The resulting soap was cut into halves, and the cut surface was evaluated with the naked eye and graded according to the following standard.

A . . . No variation in shade was observed from part to part.

B . . . A streak due to variation in shade was observed from part to part.

C . . . Streaks or areas different in shade were observed from part to part.

Evaluation of Appearance

The appearance was observed with the naked eye and graded according to the following standard.

A . . . Equal to the cavity shape

B . . . Substantially equal to the cavity shape

C . . . Sink marks were observed as compared with the cavity shape.

neither shrinkage nor sink marks attributed to cooling. The aerated soaps obtained in Examples have approximately the same weight as previously set. While not shown in the Table, the aerated soaps obtained in Examples gave off no offensive odor attributed to heating of the molten soap. To the contrary, the aerated soaps of Comparative Example 1 showed non-uniformity of bubble dispersion.

Industrial Applicability

According to the method of the present invention for producing aerated soap, molten soap having a great number of bubbles dispersed therein can be prevented from separating into gas and liquid.

According to the method of the present invention for producing aerated soap, aerated soap having bubbles uniformly dispersed therein and thereby exhibiting good latherability are obtained.

Where, in particular, molten soap is injected in an amount larger than a set volume of aerated soap, shrinkage or development of sink marks on cooling can be prevented effectively in solidifying molten soap. Further, use of an inert gas for aerating molten soap is effective in preventing generation of offensive odors attributed to heating of the molten soap.

Aerated soap products can be produced without variation in weight by adjusting the volume of molten soap to be supplied to a molding unit in accordance with the specific gravity of the molten soap to be fed.

What is claimed is:

1. A method of producing aerated soap which comprises solidifying molten soap having a large number of bubbles dispersed therein in a molding unit, wherein a circulating duct is connected to a storage tank of the molten soap to form a loop passing through said storage tank, said circulating duct or said storage tank has connected thereto a feeding section for feeding the molten soap, and the molten soap is fed to said molding unit through said feeding section while being circulated through said circulating duct.

2. The method of producing aerated soap according to claim 1, wherein the volume of the molten soap to be fed to said molding unit is adjusted according to variations in specific gravity of the molten soap to be fed to said molding unit so that the weight of the molten soap to be fed is constant.

TABLE 2

| | | Example | | | | | | Comparative |
|---|---|---|---|---|---|---|---|---|
| | | 1 | 2 | 3 | 4 | 5 | 6 | Example 1 |
| Molten Soap | Circulating Temp. (° C.) | 64 | 65 | 55 | 70 | 70 | 64 | 64 |
| | Circulating Flow Rate V ($m^3$/hr) | 3.3 | 2 | 1 | 0.5 | 0.5 | 3.3 | — |
| | Circulating Flow Velocity Vd (m/s) | 0.15 | 0.05 | 0.03 | 0.02 | 0.02 | 0.12 | — |
| | S/V (hr) | 0.06 | 0.1 | 0.2 | 0.4 | 4 | 0.06 | — |
| | Shear Rate D ($s^{-1}$) | 1.8 | 0.6 | 0.5 | 0.3 | 0.3 | 1.8 | — |
| | Injected Volume (%*) | 135 | 125 | 112 | 135 | 135 | 120 | 135 |
| Aerated Soap | Compression Ratio | 1.49 | 1.64 | 1.45 | 1.86 | 1.86 | 1.70 | 2.47 |
| | Apparent Density (g/$cm^3$) | 0.75 | 0.62 | 0.75 | 0.6 | 0.6 | 0.75 | 0.8 |
| | Pore Volume Fraction (%) | 100 | 100 | 100 | 100 | 100 | 100 | 50 |
| | Dispersed State of Bubbles | A | A | A | A | A | A | C |
| | Appearance | A | A | B | B | B | B | B |
| | Weight (g) | 90 | 90 | 90 | 90 | 90 | 90 | 90 |

Note:
*Based on a set volume of an aerated soap

As is apparent from the results shown in Table 2, the aerated soaps obtained in Examples have bubbles uniformly dispersed therein and exhibit satisfactory appearance with

3. The method of producing aerated soap according to claim 2, wherein the molten soap stored in said storage tank is fed to said molding unit in a volume adjusted according to variations of the liquid level of said molten soap in said storage tank.

4. The method of producing aerated soap according to claim 2, wherein the specific gravity of said molten soap is measured at a position between said storage tank and said molding unit.

5. The method of producing aerated soap according to claim 1, wherein the circulating molten soap is kept at a temperature of 55 to 80° C.

6. The method of producing aerated soap according to claim 5, wherein the molten soap is cooled to a temperature lower than said retained temperature before it is fed to said molding unit.

7. The method of producing aerated soap according to claim 1, wherein the circulation of the molten soap is such that the ratio of the capacity S ($m^3$) of said storage tank to the circulating flow rate V ($m^3$/hr) of the molten soap is 0.01 to 5.

8. The method of producing aerated soap according to claim 1, wherein the circulation of the molten soap is such that the molten soap has a shear rate of 0.2 to 500 $s^{-1}$.

9. The method of producing aerated soap according to claim 1, wherein said circulating duct or said storage tank has connected thereto a plurality of said feeding sections, and as many molding units as said feeding sections are used.

10. The method of producing aerated soap according to claim 1, wherein said storage tank has a plurality of said circulating ducts, each circulating duct having one or more than one feeding sections, and as many molding units as said feeding sections are used.

11. An apparatus for producing aerated soap which is used to carry out the method of producing aerated soap set forth in claim 1, which comprises a storage tank for molten soap, a circulating duct connected to said storage tank and forming a loop passing through said storage tank, a molten soap feeding section connected to said circulating duct or said storage tank, and a molding unit where the molten soap fed from said feeding section is molded and solidified into a prescribed shape.

12. The apparatus for producing aerated soap according to claim 11, wherein a heat retaining unit for keeping the molten soap circulating in said circulating duct at a prescribed retained temperature is fitted to said circulating duct and said storage tank, and a cooling unit for cooling the molten soap to a temperature lower than said retained temperature is fitted between said storage tank and said feeding section.

* * * * *